United States Patent [19]

Eriksson et al.

[11] Patent Number: 4,935,366
[45] Date of Patent: Jun. 19, 1990

[54] METHOD OF OBTAINING CELLULASE DEFICIENT STRAINS OF WHITE-ROT FUNGI

[75] Inventors: Karl-Erik Eriksson, Täby; Susanna C. Johnsrud, Lidingö, both of Sweden

[73] Assignee: Svenska Träforskningsinstitutet, Stockholm, Sweden

[21] Appl. No.: 864,730

[22] PCT Filed: Sep. 18, 1985

[86] PCT No.: PCT/SE85/00358

§ 371 Date: May 16, 1986

§ 102(e) Date: May 16, 1986

[87] PCT Pub. No.: WO86/01843

PCT Pub. Date: Mar. 27, 1986

[51] Int. Cl.$^5$ .......................... C12N 9/14; C12N 1/14; D21C 1/00; C12R 1/645

[52] U.S. Cl. ................................. 435/195; 435/254; 435/277; 435/911

[58] Field of Search ................ 435/277, 911, 195, 254

[56] References Cited

U.S. PATENT DOCUMENTS 3,962,033  8/1976  Eriksson et al. .

FOREIGN PATENT DOCUMENTS 1560022 of 0000 United Kingdom .

OTHER PUBLICATIONS

Gold, M. H. et al, Arch. Microbiol. vol. 121 (1), pp. 37–41 (1979).
Ander, P. et al, Sven. Paperstidn. vol. 78 (18), pp. 643–652 (1975).
Chemical Abstracts vol. 99 (1983), abstract No. 136 645r, Arch. Microbiol., 1973, 135(3), 161–8 (Eng.).
Cross–Breeding of Selected and Mutated Homokaryotic Strains of Phanerochaete Crysosporium K-3: New Cellulase Deficient Strains with Increased Ability to Degrade Lignin by Susanna C. Johnsrud et al; Appl Microbial Biotechnol (1985) 21:320–327.
Degradation of Lignin and Lignin Model Compounds by Various Mutants of the White–Rot Fungus Sporotrichum Pulverulentum by Karl–Erik Eriksson et al; Arch Microbiol (1983) 153:161–168.
Mikrobiologi, B. Noren (Almqvist & Wiksell, Stockholm 1970), p. 438.
Patent Cooperation Treaty International Preliminary Examination Report; PCT/SE85/00358; Receiving Office: Swedish patent Office.

Primary Examiner—Thomas G. Wiseman
Assistant Examiner—Joan Ellis
Attorney, Agent, or Firm—Oblon, Spivak, McClelland, Maier & Neustadt

[57] ABSTRACT

A method is described of obtaining cellulase deficient strains which have great ability to degrade lignin at the same time. The method comprises crossing a homokaryotic cellulase deficient mutant of a white-rot fungus having a full sexual cycle with a homokaryotic strain of the same fungus, this strain having great lignin degrading ability. Strains are subsequently selected that have great lignin degrading ability in combination with cellulase deficiency. A suitable white-rot fungis is Phanerochaete chrysosporium. The crossings are suitably performed for a plurality of generations. The strain of white-rot fungus obtained is used for delignifying lignocellulosic material.

5 Claims, 1 Drawing Sheet

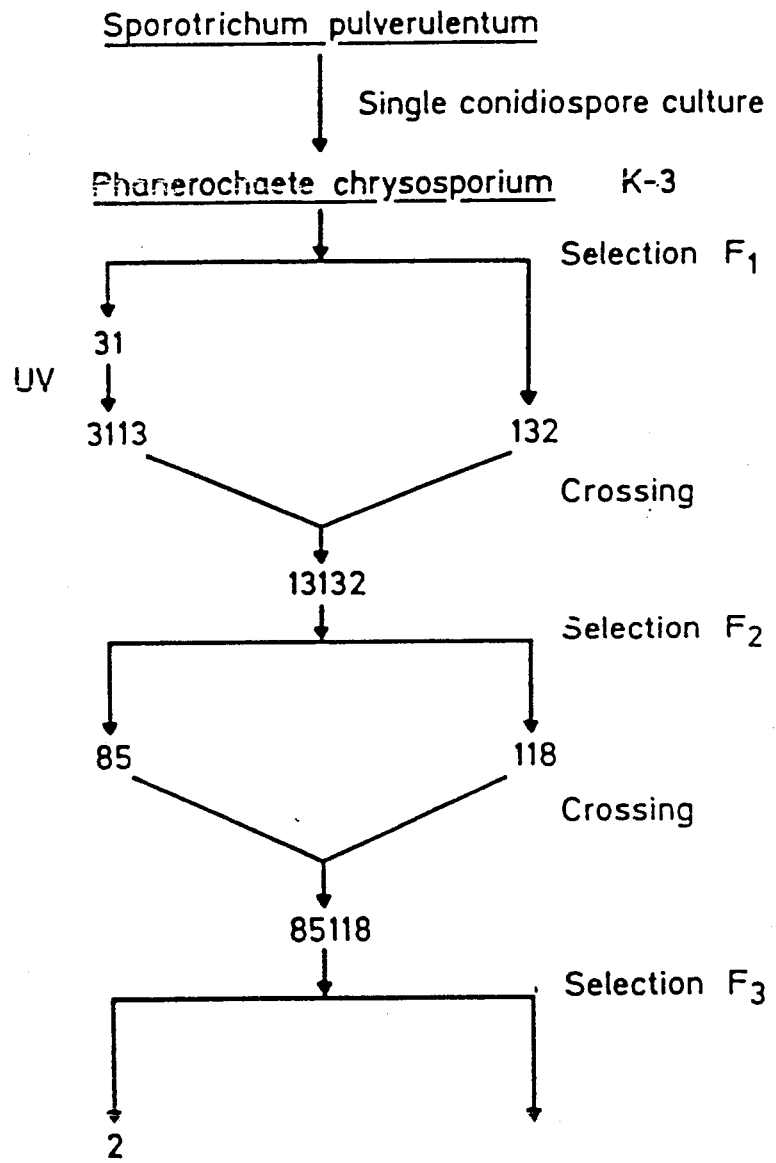

METHOD OF OBTAINING CELLULASE DEFICIENT STRAINS OF WHITE-ROT FUNGI

TITLE OF THE INVENTION

BACKGROUND OF THE INVENTION

1. Field of the Invention

The present invention relates to the delignification of raw material containing lignin and cellulose, such as wood, straw or other lignocellulosic material, while using lignin degrading organisms.

2. Description of the Related Art

It is known, e.g. from the U.S. Pat. No. 3,962,033, that it is possible to extract cellulose from wood and other raw material containing lignin and cellulose, by treating the raw material with an organism producing lignin degrading enzymes under conditions where the lignin is degraded without the cellulose being substantially affected. The organisms primarily intended in this patent are white-rot fungi, which normally produce both lignin and cellulose degrading enzymes. The patent is particularly directed to the use of the white-rot fungus *Sporotrichum pulverulentum*. According to the patent specification, treatment of the lignocellulosic material may be carried out by the addition of substances, primarily sugar, which inhibit production of cellulose degrading enzymes (cellulases) by the fungus so that mainly only the lignin degrading enzymes are active.

However, it is also possible to treat the raw material by using an artifically obtained mutant of the microorganism mentioned above, that has had its ability to form cellulases eliminated or reduced in relation to the organism present in nature. It is thus stated in the patent specification that suitable mutants of *Sporotrichum pulverulentum* may be obtained by ultraviolet irradiation or other mutagenic agents, and sorting out for pure growth the cellulase-deficient mutants thus formed.

It appears that *Sporotrichum pulverulentum*, as far as is known at present, is the best lignin degrading fungus. It has earlier been regarded as having an incomplete sexual cycle. Mutations of conidia (asexual spores) have therefore been resorted to for obtaining the cellulase-deficient mutants. It is known that basidiomycetes generally have two ways for their reproduction and survival, i.e. the sexual and the asexual form. The sexual form is characterized by the production and release of basidiospores, whereas the asexual form may involve the production of asexual spores (oidia, conidia, chlamydospores, arthrospores) which can be spread or remain in situ.

The sexual form naturally means a much larger genetic variation within the population than the asexual form.

It has now been found, however, that the cellulase-deficient mutants of *Sporotrichum pulverulentum* obtained in this way unfortunately have a substantially reduced ability to degrade lignin, compared with the wild strain. In any case, it has not been possible to obtain mutants in this way that degrade lignin (or delignify wood) to an extent sufficient for commercial utilization. This appears to be connected, inter alia, with these mutants not only being cellulase deficient but also xylanase deficient. For this reason little or no sugar is formed, which the fungus needs for producing $H_2O_2$, which is inescapably required for the lignin degradation.

SUMMARY OF THE INVENTION

The present invention aims at eliminating the drawbacks with the known technology by obtaining strains of *Sporotrichum pulverulentum* (*Phanerochaete chrysosporium* K-3), which distinguish themselves, not only by substantially reduced or even eliminated production of cellulase, but above all the retained, or even increased ability of degrading lignin.

The invention is founded on the discovery that *Sporotrichum pulverulentum* has a complicate sexual cycle, it forms basidia and basidiospores and is thus included in the Basidiomycetes. This discovery in combination, inter alia, with the development of methods for the routine production of basidiospores, development of methods for routinely testing great lignin degradation ability, methods for sorting out self-fertilising strains, and methods for testing crossing ability have enabled the use of classical genetic methods, i.e. crossing selected homokaryotic strains, for the production of organisms having the desired properties, i.e. high lignin degrading ability in combination with cellulase deficiency.

BRIEF DESCRIPTION OF THE DRAWINGS

FIG. 1 shows the process of selection and crossing of homokaryotic basidiospore cultures.

DESCRIPTION OF THE PREFERRED EMBODIMENTS

The invention thus relates to a method of producing microorganisms suitable for the delignification of wood and other lignocellulosic material, by crossing homokaryotic strains of *Phanerochaete chrysosporium* K-3 (*Sporotrichum pulverulentum*) of great lignin degrading ability with cellulase-deficient mutants obtained, for example, by ultraviolet irradiation of conidia from homokaryotic mycelia, as is more specifically stated in claim 1. These crossings are made with many generations of the fungus, better and better lignin degradation being obtained while the property of cellulase deficiency is retained.

The invention similarly relates to a method of extracting cellulose from lignocellulosic material by treatment with a lignin degrading organism, which is distinguished by the treatment being performed with a strain of *Sporotrichum pulverulentum* obtained in a way disclosed above and which is cellulase deficient, but has great lignin degrading ability.

The invention may particularly be applied to the extraction of cellulose (pulp) from wood, straw, bagasse and other lignocellulosic material by delignifying the wood with the organism intended by the invention. Accordingly, the wood, suitably in a finely divided form such as chips, is exposed to the microorganism und conditions suitable to the expansion of the latter, until the desired amount of lignin has been degraded. Depending on circumstances, this amount may vary from as low as 1% and up to nearly 100% of the lignin, while the cellulose is left substantially unaffected, and may then be extracted. The mentioned U.S. Pat. No. 3,962,033 may be referred to with regard to the treatment conditions.

Another important application of the inventively produced microorganism is its use in degrading straw, bagasse and other lignocellulosic material with the object of converting it to a more suitable product for animal feed. Wood chips, e.g. chips from aspen or poplar, may also be delignified in this way for use as animal feed.

Obtaining a cellulase deficient strain of *Sporotrichum pulverulentum* (*Phanerochaete chrysosporium* K-3) will be described in detail in the following. The treatment is based on the discovery that fruit body building and the production of basidiospores occurred in the strain used, and that the fungus is thus a basidiomycete with a full sexual cycle. It was found that fruit bodies of *Sporotrichum pulverulentum* produced basidia having 2–8 sterigmata, the dominating number being 4. In the study described here, basidiospores from basidia having four sterigmata were used in the crossing experiments. From one of these strains, designated *Phanerochaete chrysosporium* K-3, new strains were obtained by a process of selection and crossing of homokaryotic basidiospore cultures, this process being illustrated in FIG. 1. These strains were designated, for those that were cellulase deficient: 3113, 3132-85, 13132-118, 85118, and for those which were cellulase-positive: K-3, 31, 132, 13132. The cellulase deficient (Cel$^-$) strain 3113 was obtained by ultraviolet irradiation of strain 31. The cultures were maintained on fir chips (*Picea abies*).

1. Selection of monosporous strains of *S. pulverulentum*

As mentioned above, it had been found that fruit bodies of *S. pulverulentum* produced basidia having 2–8 sterigmata. This was found to complicate the crossing and interpretation of the results of crossing selected homokaryotic strains. It was observed that when selected homokaryotic mycelia derived from basidiospores from basidia having 2–8 sterigmata were crossed on birch wood meal agar medium, very few of the strains developed basidiospores. In experiments where cellulase-positive (Cel$^+$) homokaryons derived from basidiospores from basidia with only four sterigmata were crossed with cellulase deficient (Cel$^-$) strains derived from strains having varying numbers of sterigmata, only one in 85 homokaryons selected from F, was Cel$^-$. After several unsuccessful crossing and selection trials it was decided to use only basidiospores from basidia having four sterigmata in the crossing experiments. Since the germination of single conidiospores resulted in heterokaryons, it was possible to select monosporous conidiospore cultures of *S. pulverulentum* for the production of basidia having only four sterigmata.

Germinating, single conidiospores of *S. pulverulentum* were isolated after 16 hours' growth on Petri dishes containing 5 ml 3% malt extract and 2% agar, and were incubated at 39° C. Isolation was microscopically supervised to ensure that the colonies arose from separate conidiospores. When the conidiospores from these colonies were transferred to a fruit bodyinducing medium, all the examined strains showed the heterokaryotic phenotype characteristic for Phanerochaete. 20 such strains were used in experiments to determine the expansion of $^{14}CO_2$ from $^{14}C$ ring-marked synthetic lignin (as a measure of lignin degrading ability). A strain (K-3) that showed high $^{14}C_2$ expansion in these experiments was selected for continued crossing attempts.

2. Isolation of cellulase deficient strains

The homokaryotic strain 31 was selected for mutation experiments. By UV treatment of the conidiospores of this strain, and the selection of cellulase mutants using a technique known per se, several cellulase deficient strains were obtained, and one of these, Cel$^-$ strain 3113. was used in continued crossings with Cel$^+$ and Cel$^-$ strains to obtain Cel$^-$ heterokaryons that had high $^{14}CO_2$ expansion from C ring-marked lignin.

3. Crossing experiments

Monosporous basidiospore cultures were used to examine the heredity of the lignin degrading ability. Homokaryotic parents having increased ability to release $^{14}CO_2$ from $^{14}C$ ring-marked lignin, compared with K-3 were mated and selected for homokaryotic progeny.

4. Degradation of lignin in wood

The cellulase deficient strains 3113, 13132-85 13132-118 and 85 118 together with P-chrysosporium K-3 were examined in wood decomposing experiments, where wafers (2×20×50 mm) of fir (*Pices abies*) and birch (*Betula verrucosa*) were used. The weight losses, and particularly the lignin losses, were compared between the Cel$^-$mutants and the strain K-3. The result showed that K-3, which degrades the cellulose, caused a greater weight loss than the Cel$^-$ mutants However, the lignin loss caused by the mutants was, greater than that caused by K-3.

We claim:

1. A method of obtaining cellulase deficient white rot fungal strains capable of degrading lignin, which comprises:

mutating a homokaryotic strain derived from a monosporous basidiospore culture of the heterokaryotic strain *Phanerochaete chrysosporium*, wherein the parent strain produces fruit bodies having four sterigmata and has been selected from basidiospores of a monosporous conidiospore culture of *Sporotrichum pulverulentum*, which is the asexual cycle of *Phanerochaete chrysosporium*, to obtain a cellulase deficient strain, crossing the cellulase deficient strain with a natural homokaryotic strain of *Phanerochaete chrysosporium* having significant lignin degrading ability, and selecting from the progeny strains that have both the same or greater lignin degrading ability as the parent strain and substantially reduced or eliminated production of cellulase as the parent strain.

2. A method as claimed in claim 1, wherein said crossing is carried out over a plurality of generations.

3. A method of delignifying lignocellulosic material, wherein said material is contacted with a strain of white-rot fungus obtained in accordance with claim 1.

4. A method as claimed in claim 3, wherein the lignocellulosic material is wood.

5. A method as claimed in claim 3, wherein said lignocellulosic material is straw, bagasse, or a lignocellulosic agricultural waste other than bagasse.

* * * * *

UNITED STATES PATENT AND TRADEMARK OFFICE
CERTIFICATE OF CORRECTION

PATENT NO. : 4,935,366

DATED : June 19, 1990

INVENTOR(S) : Karl-Erik Eriksson et al

It is certified that error appears in the above-identified patent and that said Letters Patent is hereby corrected as shown below:

Title page, the following should be inserted.

--[30]    Foreign Application Priority Data

September 19, 1984   [SE]   Sweden..................8404698--

Signed and Sealed this

Twenty-fifth Day of June, 1991

*Attest:*

HARRY F. MANBECK, JR.

*Attesting Officer*     *Commissioner of Patents and Trademarks*